United States Patent
Kaplan et al.

(10) Patent No.: US 7,141,773 B2
(45) Date of Patent: Nov. 28, 2006

(54) IMAGE FOCUSING IN FLUORESCENT IMAGING

(75) Inventors: Eran Kaplan, Rehovot (IL); Avner Freiberger, Rishon LeZion (IL)

(73) Assignee: Bioview Ltd., Nes Ziona (IL)

( * ) Notice: Subject to any disclaimer, the term of this patent is extended or adjusted under 35 U.S.C. 154(b) by 204 days.

(21) Appl. No.: 10/485,116

(22) PCT Filed: Aug. 6, 2002

(86) PCT No.: PCT/IL02/00643

§ 371 (c)(1),
(2), (4) Date: Feb. 5, 2004

(87) PCT Pub. No.: WO03/014795

PCT Pub. Date: Feb. 20, 2003

(65) Prior Publication Data
US 2005/0056767 A1    Mar. 17, 2005

(51) Int. Cl.
*H01J 27/00* (2006.01)

(52) U.S. Cl. .................. 250/208.1; 250/201.3

(58) Field of Classification Search ............ 250/201.3, 250/208.1
See application file for complete search history.

(56) References Cited

U.S. PATENT DOCUMENTS 5,245,173 A * 9/1993 Yamana et al. .......... 250/201.3
5,790,710 A * 8/1998 Price et al. ................. 382/255

* cited by examiner

*Primary Examiner*—Que T. Le

(57) ABSTRACT

An imaging apparatus with an autofocus mechanism for obtaining focused images. The apparatus comprises: an objective lens, a focus controller for altering a distance between the objective lens and a sample, an object finder for finding objects of interest within the sample, for example cells, and a light intensity measurement unit which measures light intensity levels of the thus identified objects of interest. The focus control alters the sample-objective distance to maximize the light intensity levels being measured, thereby to arrive at a focus position. Objects of interest may be identified by filtering out large objects and optionally by masking out background regions. The apparatus is useful for microscopy and particularly for fluorescent imaging in which light levels are low and noise is often high.

73 Claims, 5 Drawing Sheets

IMAGE FOCUSING IN FLUORESCENT IMAGING

FIELD OF THE INVENTION

The present invention relates to focusing for image capture and more particularly but not exclusively to fluorescent imaging and to image focusing in high resolution scanning systems.

BACKGROUND OF THE INVENTION

In high resolution scanning systems, focusing is a major rate-limiting step in that it is not unusual to find systems which spend approximately half of the imaging time on focusing. Thus, optimizing the focusing process is important for providing system throughput. For fluorescent imaging in particular, the situation is more extreme, as will be explained below.

Conventional microscopy focus algorithms rely on the images themselves. A series of images at different focal planes is examined and the image with the largest amount of detail, or the greatest amount of information, is selected as being correctly focused. However, current systems are unable to distinguish between genuine details and noise, and thus images with high signal to noise ratio (SNR) are required for effective focusing.

Considering conventional focusing in greater detail, conventional focusing relies on the quality of the images. In order to perform the focus sequence, the system takes a series of images around an estimated focus position. For each image, the system records its position, and computes a focus score which characterizes the sharpness of the respective image. In a final step, the system computes a position for which the focus score is maximal, and the computed position is taken as the focus position.

The sharpness function is one of many functions that evaluate the amount of fine detail in an image. A good sharpness function is sensitive (a small change in the amount of detail produces a large change in the focus score), and well-behaved over a large range. That is to say, as the distance from the focus position increases, the focus score decreases, even for large distances from the focus position. Considering by way of example the following sequence:
1. take an image,
2. convolve the image with a fine detail filter (e.g. Sobel filter),
3. sum the absolute value of the intensity of pixels in the convolved image, and
4. set the focus score (FS) to the above sum.

The above sequence is repeated typically five to ten times for each one of five to ten different images and a focus position is computed, preferably by interpolation between the images to find a maximal sum position.

The main drawback to the above-described sequence, and a drawback which applies to a complete family of functions, is that they are sensitive to noise. Thus, unless image quality is good, the largest contribution for the focus score comes from the noise, and both the requirements for sensitivity and for a large range are lost Fluorescent imaging is characterized as being a low light application, meaning that only low levels of light are emitted from the sample. In addition, high resolution is needed in order to distinguish details of the sample. Thus a fluorescent imaging system is required to provide large magnification of the sample, to have a high capacity for collecting light and requires relatively long exposure times in order to obtain a reasonable image. In order to provide the high magnification necessary, high magnification objective lenses are used, typically of ×40 and above. In order to achieve the high resolution and to collect as much light as possible, objective lenses with high numerical apertures (NA), typically 0.75 and above, are generally used. Typical exposure times of the order of a second and above are needed in order to obtain high quality, low noise images.

It will be appreciated that a high NA causes a low depth of field. Thus even slight deviations in the distance between the objective and the sample can lead to severe misfocusing of the image. Conventional focusing of the kind described above typically requires five-ten images. The requirement of low noise images means that the exposure time used for focus need to be similar to that used for the actual imaging. In the case of fluorescent imaging, a focusing time of around five-ten seconds is therefore implied. Thus in fluorescent imaging the system spends the vast majority of its time focusing, and the focusing problem is an obstacle to providing a high throughput fluorescent imaging system.

SUMMARY OF THE INVENTION

The embodiments described herein overcome the difficulties explained above by removing the dependence on image details such as differential information and high frequency details, in the process of focusing. Instead, it uses the image energy, that is to say integral information and low frequency details for finding the focal position. The embodiments are thus able to be used on relatively noisy images, which can be focused rapidly. The system is particularly useful for providing fast throughput for large quantities of data.

According to a first aspect of the present invention there is an imaging apparatus for taking images of samples, the apparatus comprising:
an objective lens,
a focus controller for altering a distance between the objective lens and the sample,
an object finder for finding objects of interest within the sample, and
a light intensity measurement unit, associated with the focus controller, arranged to measure light intensity levels, gathered through the objective lens, of the objects of interest, the apparatus being operable to alter the distance to maximize the light intensity levels, thereby to find a focus position.

Preferably, the focus controller is controllable to stepwise alter the focus through a series of distances to allow the light intensity measurement unit to measure the light intensity at each of the focus distances, therefrom to select one of the focus distances giving maximum intensity as the focus position.

The apparatus may be comprised within a camera, meaning that it is configured to work with the camera objective to provide autofocus for the camera.

Typically, the sample used is a fluorescent sample, since images of fluorescent samples are typically high noise and hard to focus using conventional methods.

Preferably, the object finder comprises a small object filter for filtering to include only small objects of the sample.

Preferably, the object finder comprises a bright object filter for filtering out objects fluorescing above a predetermined fluorescing threshold.

Preferably, the object finder comprises a background filter for filtering out a background color.

Preferably, the object finder comprises a background filter for filtering out a background color.

The apparatus may further comprise a filter for filtering out objects fluorescing above a predetermined fluorescing threshold.

Preferably, the small object filter is operable to filter out regions not being objects occupying less space than substantially 500 pixels of an image.

Preferably, the light intensity measurement unit is operable to compute an average intensity over an image taken of the sample using at least a first of the focusing distances.

Preferably, the light intensity measurement unit is further operable to compute a standard deviation of the intensity over the image.

The apparatus may further comprise a thresholder associated with the light intensity measurement unit for using the average intensity and the standard deviation to compute an image threshold for thresholding pixels of the image.

Preferably, the threshold is the average intensity plus a predetermined image constant times the standard deviation.

Preferably, the thresholder is operable to compute a focusing threshold in addition to the image threshold.

Preferably, the focusing threshold is the average intensity plus a predetermined focusing constant times the standard deviation.

Preferably, the small object filter is operable to filter for the small objects by forming a mask by setting to zero any pixel that is outside of an object being smaller than a predetermined blob size.

The apparatus may further comprise a thresholder, operable to threshold an image using a brightness threshold.

Preferably, the thresholder is operable to threshold for brightness separately for color bands of the image.

Preferably, the thresholder is operable to threshold for brightness separately for color bands of the image such as to filter out a color associated with an image background, thereby to provide a background filter.

The apparatus may further comprise combination logic for ANDing the thresholded image with the mask.

The apparatus may further comprise combination logic for ANDing the thresholded image with the mask, thereby to form an image comprising delineated objects of interest.

The apparatus may further comprise a noise remover operable to set to zero each pixel of the image lacking at least one non-zero pixel as a neighbor.

Preferably, the noise remover comprises a rank filter.

The apparatus may further comprise a focus scorer for computing a focus score to an image, the focus scorer comprising a summator for summing over substantially each pixel in the image the difference, raised to the power of a predetermined constant, between the pixel intensity level and the average intensity level for the image.

The apparatus may further comprise the predetermined constant is a positive number.

Preferably, the predetermined constant is substantially 2.

The apparatus may further comprise a comparator associated with the focus scorer, for determining which of the images gives a maximum score, thereby to select an optical focus position.

The apparatus may further comprise an exposure timer having a predetermined exposure time for producing focusing images and a predetermined exposure time for producing viewing images and the predetermined exposure time for producing focusing images may typically be shorter than the predetermined exposure time for producing viewing images.

Preferably, a ratio between the exposure times is substantially between a third and a fortieth.

In a particularly preferred embodiment, the ratio between the exposure times is substantially between a tenth and a fifth.

Preferably, a ratio between the exposure times is calculable by taking substantially the square root of a ratio between a typical image SNR and an empirically determined SNR for a given focused image.

Preferably, the exposure timer is set to increase the predetermined exposure time for producing focusing images in the event of a determination of a focusing failure.

The apparatus may further comprise a comparator for determining a difference between focus scores of successive images, the apparatus being operable to reduce exposure time when the difference is above a predetermined level.

The apparatus may further comprise a focus score adjuster operable to adjust respective focus scores of focusing images to compensate for the reductions in the exposure time.

The apparatus may further comprise pixel binning functionality to increase a signal to noise ratio of the images.

The apparatus may further comprise a light intensity detector connected to a servo-unit for altering the distance, the servo-unit being controllable to alter the distance to maximize light intensity as detected by the detector.

The apparatus may further comprise a large object detector for inhibiting action of the servo-unit when the presence of a large object is detected.

The apparatus may further comprise a low magnification pre-scanner for determining whether large objects are present in the sample, and inhibiting the operation of the server unit in the presence of the large objects.

Preferably, the light intensity detection unit comprises a multi-pixel array.

According to a second aspect of the present invention there is provided a method of image focusing comprising:

illuminating a sample, collecting light from the sample via an objective lens, therefrom to form an image, identifying objects of interest within the image, and focusing the sample by altering a distance between the objective lens and the sample to maximize light intensity gathered from the identified objects of interest.

Preferably, the step of identifying objects of interest comprises filtering for small objects in the image.

According to a third aspect of the present invention there is provided a method of producing a focused image comprising:

taking a series of images, over the series filtering for small objects, over the series thresholding the images against a threshold brightness level, summing intensities of each filtered and thresholded image to form a focusing score for each image, and selecting a focusing distance substantially corresponding to that of an image having a maximum focusing score.

According to a fourth aspect of the present invention there is provided an autofocus device for use in imaging, the device comprising:

an objective lens being controllably focusable on the sample by altering a distance between the lens and the sample, an object identifier for identifying regions of interest within an unfocused image of the sample, and a light intensity measurement unit arranged to measure light intensity levels of the objects of interest gathered by the objective lens, and wherein the autofocus device is operable to alter the distance to maximize the measured light intensity levels.

Preferably, the altering of the distance comprises altering the distance stepwise to measure the light intensity at each of the steps and to select a one of the steps giving maximum intensity as a focus distance.

Preferably, the object identifier comprises a small object filter for filtering for small objects of the sample.

Preferably, the small object filter comprises a blob analyzer having a predetermined blob size, for recognizing objects that do not exceed the predetermined blob size.

Preferably, the predetermined blob size is substantially 500 pixels.

Preferably, the light intensity measurement unit is operable to compute an average intensity over an image taken of the sample using at least a first of the focus steps.

Preferably, the light intensity measurement unit is further operable to compute a standard deviation of the intensity over the image.

The autofocus device may further comprise a thresholder, associated with the light intensity measurement unit, for using the average intensity and the standard deviation to compute an image intensity threshold for thresholding pixels of the image.

Preferably, the image intensity threshold is the average intensity plus a predetermined image constant times the standard deviation.

Preferably, the thresholder is operable to compute a focusing threshold in addition to the image threshold.

Preferably, the focusing threshold is the average intensity plus a predetermined focusing constant times the standard deviation.

Preferably, the small object filter is operable to form a mask from an image taken at a predetermined focus position by setting to zero any pixel not being part of an object that is smaller than a predetermined large object threshold.

The autofocus device may further comprise combination logic for ANDing the thresholded image with the mask, thereby to form an image delineating the objects of interest.

The autofocus device may further comprise a noise remover operable to set to zero each pixel of the image lacking at least one non-zero pixel as a neighbor.

Preferably, the noise remover comprises a rank filter.

The autofocus device may further comprise a focus scorer for computing a focus score to an image, the focus scorer comprising a summator for summing over substantially each pixel in the image the difference, raised to the power of a predetermined constant, between the pixel intensity level and the average intensity level for the image.

The autofocus device may further comprise the predetermined constant is a positive number.

Preferably, the predetermined constant is substantially 2.

The autofocus device may further comprise a comparator, associated with the focus scorer, for determining which of the images gives a maximum score, thereby to alter the distance to a distance corresponding to the position to focus the sample.

The autofocus device may further comprise an exposure timer having a predetermined exposure time for producing focusing images and a predetermined exposure time for producing viewing images. The predetermined exposure time for producing focusing images is preferably arranged to be shorter than the predetermined exposure time for producing viewing images.

Preferably, a ratio between the exposure times is substantially between a fifth and a fortieth.

In a particularly preferred embodiment, the ratio between the exposure times is substantially between a tenth and a twentieth.

Preferably, the ratio between the exposure times is obtainable by taking the square root of a ratio between a typical image SNR and an empirically determined SNR for a given focused image.

Preferably, the exposure timer is set to increase the predetermined exposure time for producing focusing images in the event of a determination of a focusing failure.

The autofocus device may further comprise a comparator for determining a difference between focus scores of successive images, the apparatus being operable to reduce exposure time when the difference is above a predetermined level.

The autofocus device may further comprise a focus score adjuster operable to adjust respective focus scores of focusing images to compensate for the reductions in the exposure time.

The autofocus device may further comprise pixel binning functionality to increase a signal to noise ratio of the images.

The autofocus device may further comprise a low magnification pre-scanner for determining whether large objects are present in a sample to be imaged, and inhibiting the operation of the server unit in the presence of the large objects.

Preferably, the light intensity detection unit comprises a multi-pixel array.

According to a fifth aspect of the present invention there is provided an autofocus device for a fluorescence imaging microscope, the device comprising an image filter for filtering an image to delineate objects of interest and a light intensity measurement unit associated with a focusing mechanism for focusing by altering a focus distance to maximize measured light intensity of the filtered image.

The device may carry out the focusing using image data gathering at a lower data level than a data level needed for imaging.

BRIEF DESCRIPTION OF THE DRAWINGS

For a better understanding of the invention, and to show how the same may be carried into effect, reference will now be made, purely by way of example, to the accompanying drawings, in which.

DESCRIPTION OF THE PREFERRED EMBODIMENTS

Figure 1:
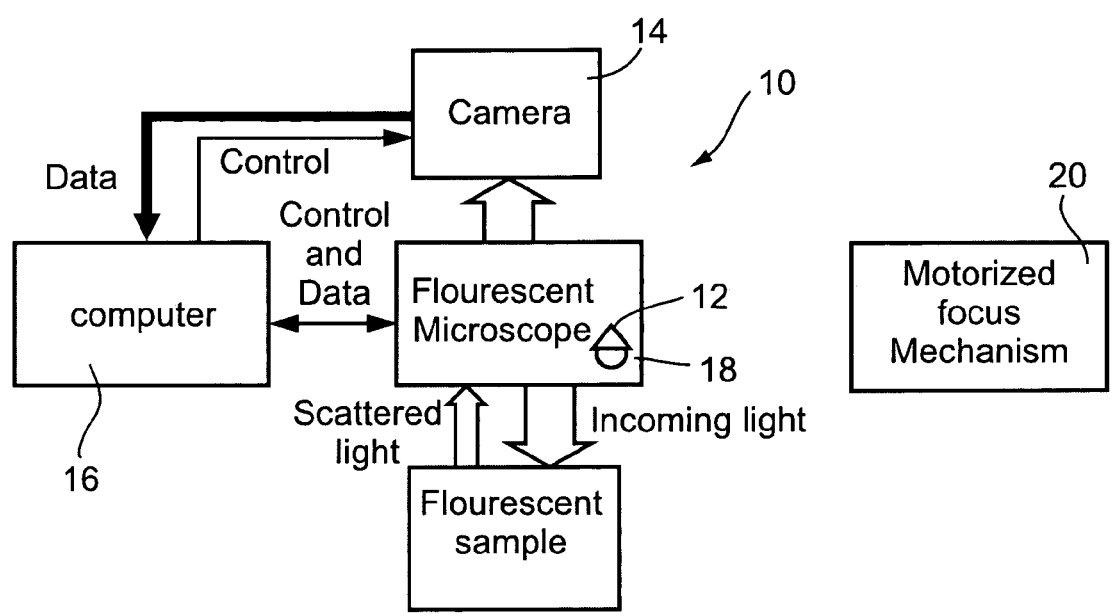
FIG. 1 is a generalized diagram showing a fluorescent imaging apparatus for taking images of fluorescing samples.

Reference is now made to FIG. 1, which is a generalized diagram showing fluorescent imaging apparatus for taking images of fluorescing samples. An apparatus 10 comprises a fluorescent microscope 12, connected to a camera 14 and to a motorized focus mechanism 20, all of which are connected to a computer 16. The computer is preferably connected to receive data from and to control both the camera and the motorized focus 20. The microscope 12 preferably comprises an illumination source 18 for illuminating a fluorescent sample. Emitted, reflected and fluorescent light is received back at the microscope 12.

As is common in microscopy, the illumination source 18 is preferably situated behind the objective lens of microscope 12, so as to illuminate the sample via the objective lens. Such a form of illumination has two effects, firstly that it concentrates illumination in the focal plane and secondly that it reduces noise in the image since the microscope picks up only emitted light and not transmitted light.

Preferably, the apparatus is provided with a light intensity measurement unit 20 arranged to measure light intensity levels of the sample as gathered by the objective lens. Preferably the light intensity is measured on a per pixel basis.

Preferably, the light intensity measurement unit is associated with control of the distance between the objective lens and the sample. Generally the sample, or more precisely the sample mounting stage is moved, in order to carry out focusing. In principle it is also possible to move the objective lens, but such is not usually done. The distance is controlled in response to light intensity measurements, preferably using motorized focus mechanism 20. As mentioned above, the use of the objective lens as a route for the illumination light ensures that the image is most highly illuminated when it is in the focal plane. Thus, measured light intensity reaches a maximum when the sample is in the focal plane of the objective lens. Hence it is possible to control changes of the focus distance to maximize the intensity signal, thereby focusing on the sample.

The above principle works as long as the sample is not large relative to the field of view. If the sample is large than it has the effect of integrating the light signal to give an overall light intensity which is high even when the sample is not focused. Methods for removing large objects from consideration will be discussed below.

In one preferred embodiment of the present invention a focusing procedure is carried out in which the camera is set to a fast exposure rate and then a series of images are taken. Light intensity is measured at each image to determine an image which has a maximum light intensity. The motorized focus is moved to a position corresponding to the image having the maximum light intensity and the microscope is now focused.

Figure 2:
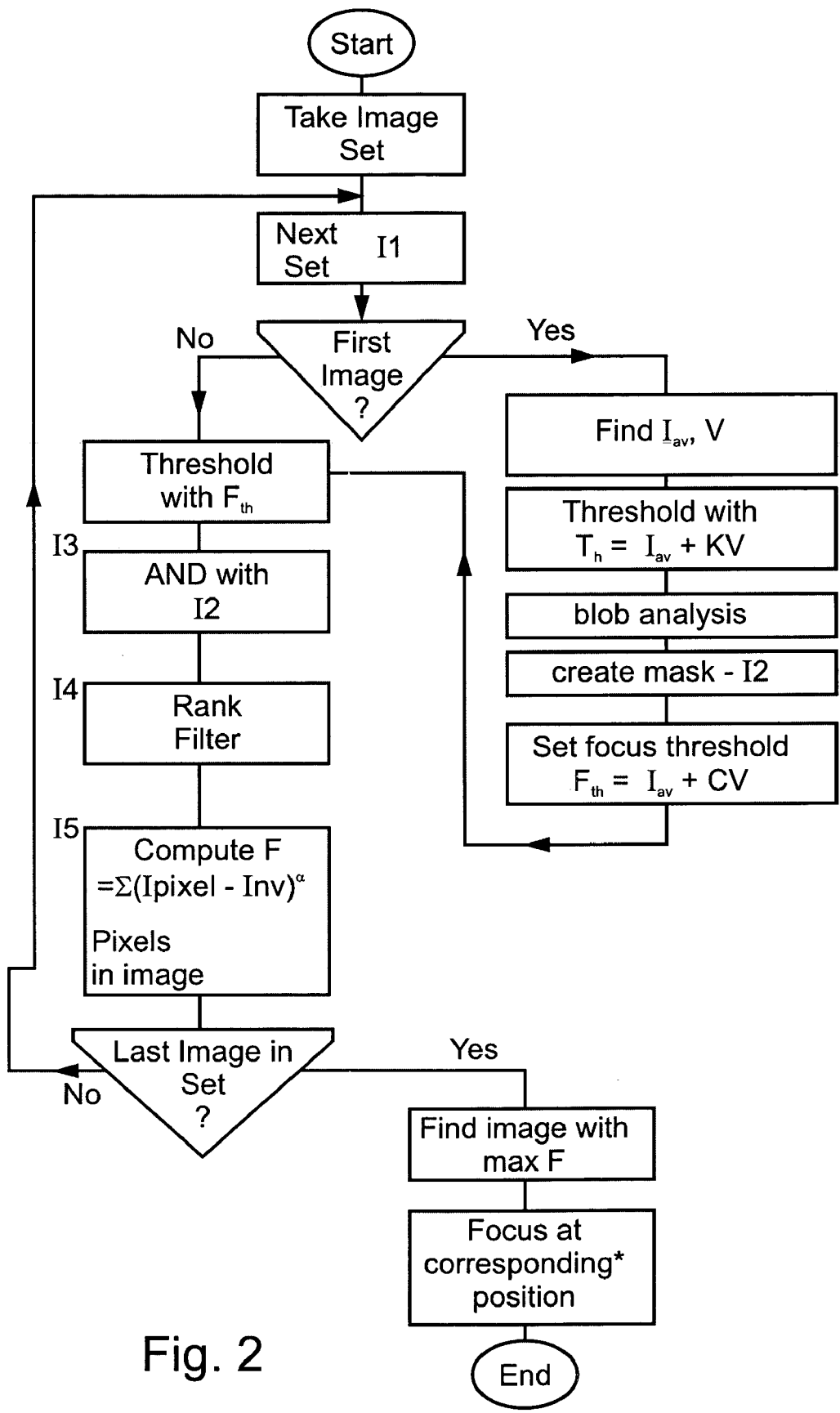
FIG. 2 is a simplified flow chart showing a method of focusing using a preferred embodiment of the present invention.

Referring now to FIG. 2, the focusing procedure of the above embodiment is discussed in more detail as follows:

First of all the camera is set to its focus parameters, namely to a setting of fast exposure and high gain, and a set of images is taken at different focusing positions.

A first image is then set as (I1).

The following procedure is then carried out with the first image to obtain threshold levels and a mask to remove large objects and keep only small objects.

The average intensity $I_{av}$ and standard deviation, $\sigma$; are computed for the first image.

The image is thresholded using the image threshold $T_h = I_{av} + k*\sigma$, where k is a constant. A typical value for k would be 3.

Removal of large objects from the image is carried out using a process known as blob analysis.

In blob analysis, blobs, that is relatively uniform areas that are smaller than a given size, are identified. Typically, the size is measured in terms of pixels of the image size, and a typical size, represented by a parameter A, may be 500 pixels. Thus, a mask is generated of blobs smaller than A (A=500); a value of 1 is assigned to all pixels outside the blobs, and 0 to all pixels in the blob. The mask thereby produced is referred to as image I2.

I2 is logically "anded" with I1. The values of $I_{av}$ and of $\sigma$ are recalculated.

A focus threshold is computed using $F_{th} = I_{av} + c*\sigma$, where c is a constant. A typical value for c is 3.5.

Then, for all images including the first, the following procedure is carried out.

The respective image (I1) is thresholded using the focusing threshold $F_{th}$. That is to say 0 is assigned to all pixels below $F_{th}$, and all other pixels are left unchanged. The new image is referred to hereinbelow as I3.

A logical AND is then carried out of thresholded image I3 and mask I2. The skilled person will appreciate that the order of the thresholding and ANDing steps may be switched. The result is referred to herein as I4.

I4 is cleaned of random noise, preferably by requiring that each pixel in I4 has at least one non-zero neighbor. Such cleaning may be achieved by performing a rank filter on I4. The resulting image is referred to herein as I5.

The focus score, F may then be computed as $$F = \Sigma_{all\ image\ pixels} (I_{pixel} - I_{av})^\alpha,$$

where $I_{pixel}$ is the gray level of the pixel in I5, and $\alpha$ is a positive number, typically $\alpha = 2$.

The actual focus position is then taken to be the position corresponding to the image having maximal focus score.

Filtering for small objects using blob analysis leads to identification of two types of objects, cell objects and non-cell objects. It is possible to filter out the non-cell objects using the following procedure. Generally any given slide is likely to have a uniform background color, and it is possible, in a color image, to filter out the background color. In the thresholding stage above, it is possible to carry out thresholding according to color bands and to filter out entirely the color corresponding to the background. Such a technique thus ensures that the final image comprises small objects that do not share the non-cell background color, that is to say it includes the objects likely to be of interest to the biologist.

For a monochrome image, the filtering out of the background is still possible but is more complex since it has to be based on recognizing uniformity in gray level and texture.

As mentioned above, the exposure times during focusing may be considerably lower than the exposure times necessary for achieving a full viewing image. The reduction is due to the procedure above mentioned. An exposure timer may use a predetermined reduced exposure time set at between a fortieth and a third, and preferably between a fifth and a tenth, of the regular exposure time.

In a further preferred embodiment of the present invention a fixed ratio between exposure times is dispensed with and instead, image statistics are used to set the exposure times. For example a useful ratio is obtained by taking a typical image SNR. An empirically determined SNR is defined for a focused image and the ratio between the two is calculated. The square root of the calculated ratio is then used as the ratio between the exposure times.

In a further preferred embodiment, the exposure timer may be set such that, in the event of a failure to focus, the focusing exposure time is increased. Generally, a characteristic of fluorescent images is a cluster of bright pixels around the region of a positive signal. The above-described use of the rank filter accentuates the characteristic. An image not carrying very much information is unlikely to have pixel clustering and thus the rank filter is liable to remove much of the light in the image, giving such an image a very low focusing score. Such a low score may be recognized as a failure to focus, encouraging an increase in focus time as described.

Figure 3:
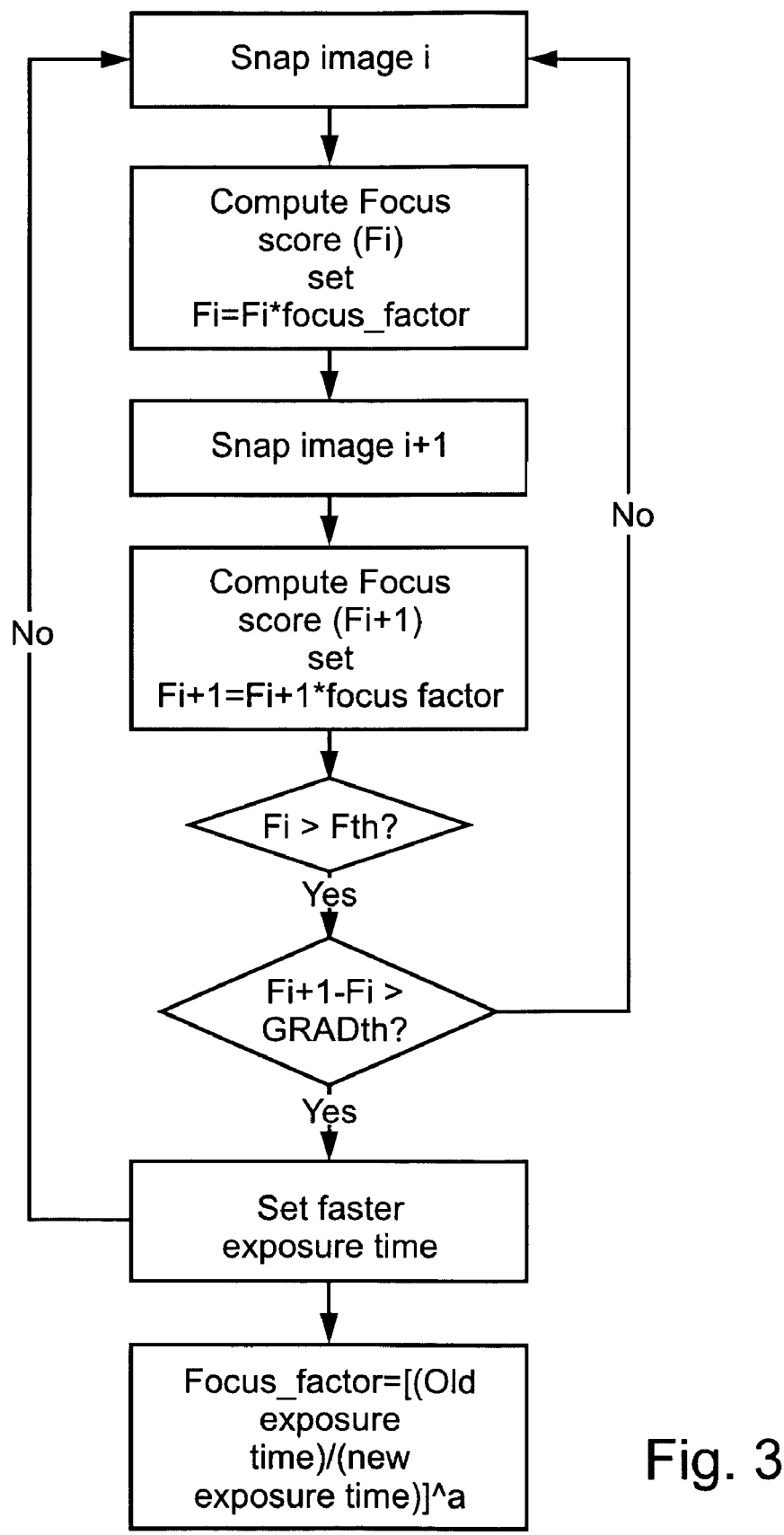
FIG. 3 is a simplified flow chart showing a preferred method for dynamically selecting an exposure time in accordance with a preferred embodiment of the present invention.

On the other hand, in the event of a surfeit of information, the opposite procedure may be followed. With reference now to FIG. 3, in a preferred embodiment a large difference between the scores of succeeding images in a series is recognized as a sign of having more than sufficient information. Thus the apparatus may reduce exposure time. It is appreciated that in using results from images with different exposure times the scores are preferably weighted with a factor to render them comparable. Thus if one image has an exposure time of a tenth of a second and the following image is taken using an exposure time of a twentieth of a second, the score of the second image is calibrated so as to be comparable to that of the first image.

Considering FIG. 3 in more detail, a first image is taken and a focus score is computed. The score is multiplied by a focus factor, currently 1. A second image is then taken and a score computed. Again the score is multiplied by the focus factor which is still 1. The second score is subtracted from the first score and the result is compared with a threshold gradient GRAD. If the threshold is exceeded, and the first focus score is larger than a predefined threshold score, a faster exposure time is set and the focus factor is updated to be the ratio between the old and the new exposure times to the power $\alpha$, wherein $\alpha$ is as defined hereinabove.

Certain cameras are provided with what is known as a pixel binning feature (sometimes called also meta-pixel or super-pixel). The feature takes an internal group of pixels and treats this group as a single pixel. The effect of pixel binning is to decrease resolution and at the same time to increase SNR. Pixel binning can be helpful in the focusing procedure as outlined above since the resolution has no effect on the above-described focusing procedure, while increased SNR may further shorten the exposure times. Thus, as long as the pixel binning does not interfere with the identification of large objects then it may usefully be incorporated into the focusing procedure.

A simplified embodiment of the present invention may use the detected light level to directly operate the motorized focus 22 in the direction of increasing light level until a peak is determined. In this case, any light meter can be used (e.g. a photodiode, avalanche photodiode or a photomultiplier). Such a simplified embodiment of the invention is sufficient as long as there are no large objects in the vicinity. Thus, in a preferred embodiment, a large object detector, for example the blob analyzer discussed above, may be used as a switch between such a simplified embodiment and an embodiment involving the masking etc procedure outlined above. Alternatively switching can be carried out using a low magnification pre-scanner. The low magnification pre-scanner preferably uses a low magnification small NA objective lens to produce a pre-scan image, which is then fed to the computer 16. The computer 16 is able to determine whether large objects are present in the sample, and to select accordingly between the simplified and the more complex embodiments.

In one preferred embodiment, the light intensity detection unit is made up of a multi-pixel detector array, for example a 4×4 array. Using such an array is the equivalent of using ultra-low resolution imaging. The array has the effect of discarding regions where large objects are present, and using information coming only from relevant areas. Nevertheless, real-time focusing is still possible.

A minimal system may be built from a fluorescent imager that can change the distance between the objective and the sample in a controlled manner. A prototype was built using a Zeiss Axioplan2 microscope, a Sony DXC9000 CCD camera, and a standard general-purpose computer. In order to test the prototype a biological sample was stained with a specific fluorescent DNA probe.

The computer controls the camera and the distance between the sample and the objective, grabs images from the camera and analyzes the results. A typical focus sequence begins when the computer determines the initial distance Z0 between the objective and the sample. The computer sets the Z0 distance and grabs an image from the camera. The image is analyzed and a focus score F0 for the current image is computed. The computer than sets another distance Z1, grabs an image and computes its score F1. This sequence is repeated until it is possible to select a position $F_{focus}$ where a peak in the focus score is found, as described above.

Figure 5:
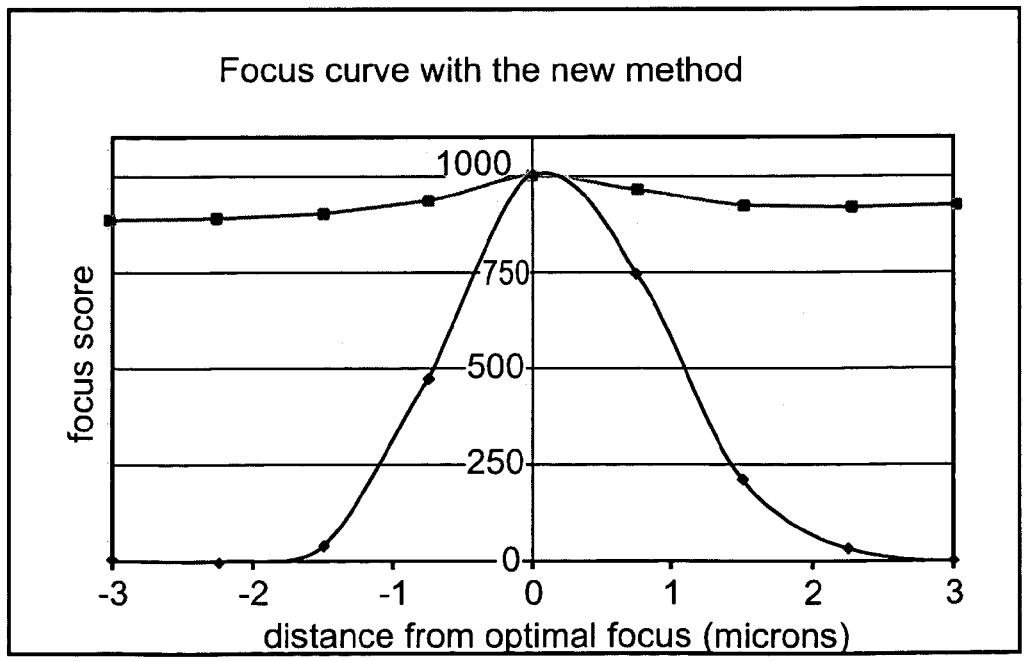
FIG. 5 is a focusing curve obtained using a system according to a preferred embodiment of the present invention.
Figure 6:
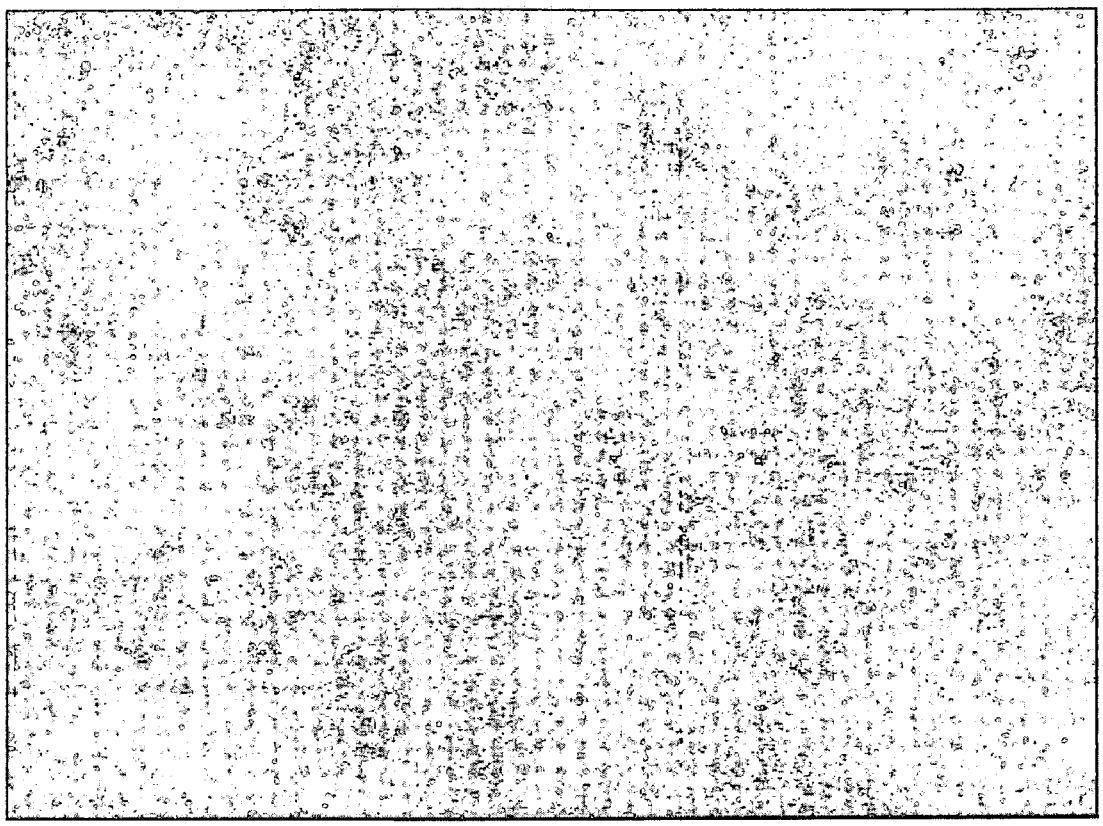
FIG. 6 is an image obtained during the focusing process according to an embodiment of the present invention, multiplied ten times for viewing.

In a test example to compare the performance of the traditional and the new focus methods, images were taken at different positions, and a focus curve was computed using each method. The sample was a regular blood sample, stained for the sex chromosomes using probes produced by Vysis Ltd. The final images were taken with an exposure time of 2 seconds. FIGS. 5 and 6 show typical focus curves on an image. The focus images when focusing using an embodiment of the invention were taken with an exposure time of 100 mSec only, 20 times faster than for the conventional method.

Figure 4:
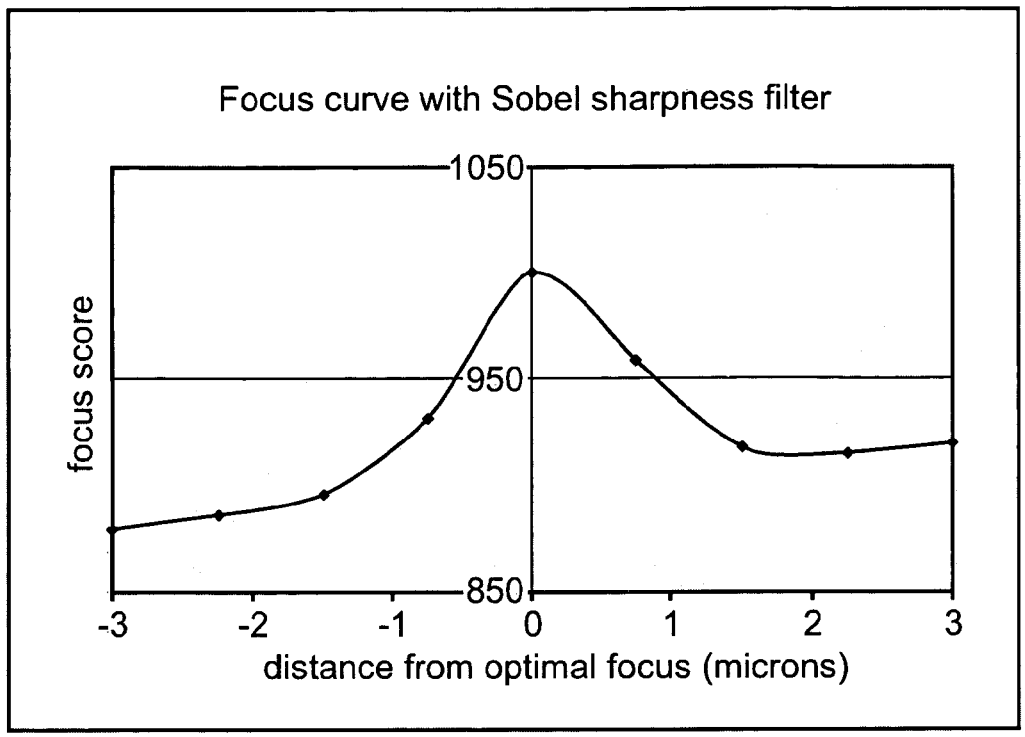
FIG. 4 is a focusing curve achieved using a prior art system.

Reference is now made to FIG. 4, which is a graph showing a focus curve for the above example using a prior art focusing system. In the graph a focus score produced by the filter, in this case a Sobel sharpness filter, is traced against distance from optimal focus. It is noticeable that there is a noticeable peak in the region of −1.5 to 1.5 microns from optimal focus, in which the focus score raises from around 900 to around 1000. Outside the above-mentioned region there is very little change in the score. Thus the score at 3 microns from optimal focus is practically the same as the score at 2 microns.

Reference is now made to FIG. 5, which is a graph showing a focus curve as produced by embodiments of the present invention. In FIG. 5, again focus score is plotted against distance from optimal focus. This time the focus score in the same region, −1.5 to 1.5 microns, varies between 50 and 1000, which is to say that the discrimination of the system is considerably higher. Also, outside the region there are noticeable differences in scores. The score drops between 2 and 3 microns!

Reference is now made to FIG. 6, which shows an image obtained during the focusing process using an embodiment of the present invention. The image that is shown and used is the clearest of the respective set of focusing images. To enable viewing, the gray levels of the original image have been multiplied by 10. It will be noticed that the image itself has a high level of noise, making standard focusing methods ineffective.

There is thus provided, according to the above embodiments, a focusing unit for fluorescent microscopy, which is able to carry out automatic focusing on a high noise image of the kind typical of fluorescent imaging.

It is appreciated that features described only in respect of one or some of the embodiments are applicable to other embodiments and that for reasons of space it is not possible to detail all possible combinations. Nevertheless, the scope of the above description extends to all reasonable combinations of the above-described features.

The present invention is not limited by the above-described embodiments, which are given by way of example only. Rather the invention is defined by the appended claims.

We claim:

1. An imaging apparatus for taking images of samples, the apparatus comprising:
   an objective lens,
   a focus controller for altering a distance between said objective lens and said sample,
   an object finder for finding objects of interest within said sample,
   a light intensity measurement unit, associated with said focus controller, arranged to calculate the sum of light intensity levels, gathered through said objective lens, of said objects of interest, said apparatus being operable to alter said distance to maximize said calculated sum of light intensity levels, thereby to find a focus position.

2. The imaging apparatus of claim 1, wherein said focus controller is controllable to stepwise alter said focus through a series of distances to allow said light intensity measurement unit to measure said light intensity at each of said focus distances, therefrom to select one of said focus distances giving maximum intensity as said focus position.

3. The imaging apparatus of claim 1, being comprised within a camera.

4. The imaging apparatus of claim 1, where said sample is a fluorescent sample.

5. The imaging apparatus of claim 1, wherein said object finder comprises a small object filter for filtering to include only small objects of said sample.

6. The imaging apparatus of claim 4, wherein said object finder comprises a bright object filter for filtering out objects fluorescing above a predetermined fluorescing threshold.

7. The fluorescent imaging apparatus of claim 4, wherein said object finder comprises a background filter for filtering out a background color.

8. The fluorescent imaging apparatus of claim 6, wherein said object finder comprises a background filter for filtering out a background color.

9. The imaging apparatus of claim 1, further comprising a filter for filtering out objects fluorescing above a predetermined fluorescing threshold.

10. The imaging apparatus of claim 5, wherein said small object filter is operable to filter out regions not being objects occupying less space than substantially 500 pixels of an image.

11. The imaging apparatus of claim 3, wherein said light intensity measurement unit is operable to compute an average intensity over an image taken of said sample using at least a first of said focusing distances.

12. The imaging apparatus of claim 11, wherein said light intensity measurement unit is further operable to compute a standard deviation of said intensity over said image.

13. The imaging apparatus of claim 12, further comprising a thresholder associated with said light intensity measurement unit for using said average intensity and said standard deviation to compute an image threshold for thresholding pixels of said image.

14. The imaging apparatus of claim 13, wherein said threshold is the average intensity plus a predetermined image constant times the standard deviation.

15. The imaging apparatus of claim 13, wherein said thresholder is operable to compute a focusing threshold in addition to said image threshold.

16. The imaging apparatus of claim 15, wherein said focusing threshold is the average intensity plus a predetermined focusing constant times the standard deviation.

17. The imaging apparatus of claim 5, wherein said small object filter is operable to filter for said small objects by forming a mask by setting to zero any pixel that is outside of an object being smaller than a predetermined blob size.

18. The imaging apparatus of claim 17, further comprising a thresholder, operable to threshold an image using a brightness threshold.

19. The imaging apparatus of claim 18, wherein said thresholder is operable to threshold for brightness separately for color bands of said image.

20. The imaging apparatus of claim 19, wherein said thresholder is operable to threshold for brightness separately for color bands of said image such as to filter out a color associated with an image background, thereby to provide a background filter.

21. The imaging apparatus of claim 17, further comprising combination logic for ANDing said thresholded image with said mask.

22. The imaging apparatus of claim 20, further comprising combination logic for ANDing said thresholded image with said mask, thereby to form an image comprising delineated objects of interest.

23. The imaging apparatus of claim 21, further comprising a noise remover operable to set to zero each pixel of said image lacking at least one non-zero pixel as a neighbor.

24. The imaging apparatus of claim 23, wherein said noise remover comprises a rank filter.

25. The imaging apparatus of claim 24, further comprising a focus scorer for computing a focus score to an image, the focus scorer comprising a summator for summing over substantially each pixel in the image the difference, raised to the power of a predetermined constant, between the pixel intensity level and the average intensity level for the image.

26. The imaging apparatus of claim 25, wherein said predetermined constant is a positive number.

27. The imaging apparatus of claim 26, wherein said predetermined constant is substantially 2.

28. The imaging apparatus of claim 27, further comprising a comparator associated with said focus scorer, for determining which of said images gives a maximum score, thereby to select an optical focus position.

29. The imaging apparatus of claim 1, comprising an exposure timer having a predetermined exposure time for producing focusing images and a predetermined exposure time for producing viewing images and wherein said predetermined exposure time for producing focusing images is shorter than said predetermined exposure time for producing viewing images.

30. The imaging apparatus of claim 29, wherein a ratio between said exposure times is substantially between a third and a fortieth.

31. The imaging apparatus of claim 29, wherein a ratio between said exposure times is substantially between a tenth and a fifth.

32. The imaging apparatus of claim 29, wherein a ratio between said exposure times is calculable by taking substantially the square root of a ratio between a typical image SNR and an empirically determined SNR for a given focused image.

33. The imaging apparatus of claim 29, said exposure timer being set to increase said predetermined exposure time for producing focusing images in the event of a determination of a focusing failure.

34. The imaging apparatus of claim 25, comprising a comparator for determining a difference between focus scores of successive images, said apparatus being operable to reduce exposure time when said difference is above a predetermined level.

35. The imaging apparatus of claim 34, further comprising a focus score adjuster operable to adjust respective focus scores of focusing images to compensate for said reductions in said exposure time.

36. The imaging apparatus of claim 1, further comprising pixel binning functionality to increase a signal to noise ratio of said images.

37. The imaging apparatus of claim 1, comprising a light intensity detector connected to a servo-unit for altering said distance, said servo-unit being controllable to alter said distance to maximize light intensity as detected by said detector.

38. The imaging apparatus of claim 37, further comprising a large object detector for inhibiting action of said servo-unit when the presence of a large object is detected.

39. The imaging apparatus of claim 37, comprising a low magnification pre-scanner for determining whether large objects are present in the sample, and inhibiting the operation of said server unit in the presence of said large objects.

40. The imaging apparatus of claim 1, said light intensity detection unit comprising a multi-pixel array.

41. A method of image focusing comprising:
illuminating a sample,
collecting light from said sample via an objective lens, therefrom to form an image,
thresholding said image against a threshold brightness level,
identifying objects within said image of brightness higher than said threshold brightness level,
filtering small objects of interest within said bright objects,
creating an image mask including only said filtered small objects of interest,
summing subsequent image intensities of each of said small objects substantially corresponding to objects of said mask, to calculate a focusing score
altering a distance between said objective lens and said sample and repeatedly calculating said focusing score for each image taken after said distance has been altered: selecting a focusing distance substantially corresponding to that of an image having a maximum calculated focusing score.

42. A method of producing a focused image comprising:
taking a series of images,
over said series filtering for small objects,
over said series thresholding said images against a threshold brightness level,
summing intensities of each filtered and thresholded image to form a focusing score for each image, and, using said summed intensities, selecting a focusing distance substantially corresponding to that of an image having a maximum focusing score.

43. An autofocus device for use in imaging, the device comprising:
an object identifier for identifying regions of interest within an unfocused image of said sample, and
a light intensity measurement unit arranged to measure light intensity levels of said objects of interest and summate said measured light intensity, and wherein said autofocus device is operable to alter said distance to maximize said summated measured light intensity levels of said objects of interest.

44. The autofocus device of claim 43, wherein said altering of said distance comprises altering said distance stepwise to measure said light intensity at each of said steps and to select a one of said steps giving maximum intensity as a focus distance.

45. The autofocus device of claim 43, wherein said object identifier comprises a small object filter for filtering for small objects of said sample.

46. The autofocus device of claim 43, wherein said small object filter comprises a blob analyzer having a predetermined blob size, for recognizing objects that do not exceed said predetermined blob size.

47. The autofocus device of claim 46, wherein said predetermined blob size is substantially 500 pixels.

48. The autofocus device of claim 44, wherein said light intensity measurement unit is operable to compute an average intensity over an image taken of said sample using at least a first of said focus steps.

49. The autofocus device of claim 48, said light intensity measurement unit further being operable to compute a standard deviation of said intensity over said image.

50. The autofocus device of claim 49, further comprising a thresholder associated with said light intensity measurement unit for using said average intensity and said standard deviation to compute an image intensity threshold for thresholding pixels of said image.

51. The autofocus device of claim 50, wherein said image intensity threshold is the average intensity plus a predetermined image constant times the standard deviation.

52. The autofocus device of claim 50, wherein said thresholder is operable to compute a focusing threshold in addition to said image threshold.

53. The autofocus device of claim 52, wherein said focusing threshold is the average intensity plus a predetermined focusing constant times the standard deviation.

54. The autofocus device of claim 45, wherein said small object filter is operable to form a mask from an image taken at a predetermined focus position by setting to zero any pixel not being part of an object that is smaller than a predetermined large object threshold.

55. The autofocus device of claim 54, further comprising combination logic for ANDing said thresholded image with said mask, thereby to form an image delineating said objects of interest.

56. The autofocus device of claim 55, further comprising a noise remover operable to set to zero each pixel of said image lacking at least one non-zero pixel as a neighbor.

57. The autofocus device of claim 56, wherein said noise remover comprises a rank filter.

58. The autofocus device of claim 57, further comprising a focus scorer for computing a focus score to an image, the focus scorer comprising a summator for summing over substantially each pixel in the image the difference, raised to the power of a predetermined constant, between the pixel intensity level and the average intensity level for the image.

59. The autofocus device of claim 58, wherein said predetermined constant is a positive number.

60. The autofocus device of claim 59, wherein said predetermined constant is substantially 2.

61. The autofocus device of claim 60, further comprising a comparator associated with said focus scorer, for determining which of said images gives a maximum score, thereby to alter said distance to a distance corresponding to said position to focus said sample.

62. The autofocus device of claim 43, comprising an exposure timer having a predetermined exposure time for producing focusing images and a predetermined exposure time for producing viewing images and wherein said predetermined exposure time for producing focusing images is shorter than said predetermined exposure time for producing viewing images.

63. The autofocus device of claim 62, wherein a ratio between said exposure times is substantially between a fifth and a fortieth.

64. The autofocus device of claim 62, wherein a ratio between said exposure times is substantially between a tenth and a twentieth.

65. The autofocus device of claim 62, wherein a ratio between said exposure times is obtainable by taking the square root of a ratio between a typical image SNR and an empirically determined SNR for a given focused image.

66. The autofocus device of claim 62, said exposure timer being set to increase said predetermined exposure time for producing focusing images in the event of a determination of a focusing failure.

67. The autofocus device of claim 58, comprising a comparator for determining a difference between focus scores of successive images, said apparatus being operable to reduce exposure time when said difference is above a predetermined level.

68. The autofocus device of claim 67, further comprising a focus score adjuster operable to adjust respective focus scores of focusing images to compensate for said reductions in said exposure time.

69. The autofocus device of claim 43, further comprising pixel binning functionality to increase a signal to noise ratio of said images.

70. The autofocus device of claim 43, comprising a low magnification pre-scanner for determining whether large objects are present in a sample to be imaged, and inhibiting the operation of said server unit in the presence of said large objects.

71. The autofocus device of claim 43, wherein said light intensity detection unit comprises a multi-pixel array.

72. An autofocus device for a fluorescence imaging microscope, the device comprising an image filter for filtering an image to delineate objects of interest and a light intensity measurement unit associated with a focusing mechanism for focusing by altering a focus distance to maximize a calculated sum of measured light intensity of said filtered image.

73. The autofocus device of claim 72, being operable to carry out said focusing using image data gathering at a lower data level than a data level needed for imaging.

* * * * *

UNITED STATES PATENT AND TRADEMARK OFFICE
CERTIFICATE OF CORRECTION

PATENT NO. : 7,141,773 B2  
APPLICATION NO. : 10/485116  
DATED : November 28, 2006  
INVENTOR(S) : Eran Kaplan et al.

Page 1 of 1

It is certified that error appears in the above-identified patent and that said Letters Patent is hereby corrected as shown below:

Priority Data:

On Title Page, insert in the section marked

--Related U.S. Application Data

Item [60] US Provisional Application No. 60/309,779 filed on August 6, 2001--

Signed and Sealed this

Twenty-seventh Day of March, 2007

JON W. DUDAS  
*Director of the United States Patent and Trademark Office*